United States Patent
Boussignac

(10) Patent No.: US 8,375,946 B2
(45) Date of Patent: Feb. 19, 2013

(54) DEVICE FOR RESPIRATORY ASSISTANCE

(76) Inventor: Georges Boussignac, Antony (FR)

(*) Notice: Subject to any disclaimer, the term of this patent is extended or adjusted under 35 U.S.C. 154(b) by 850 days.

(21) Appl. No.: 12/469,262

(22) Filed: May 20, 2009

(65) Prior Publication Data

US 2010/0229862 A1    Sep. 16, 2010

(30) Foreign Application Priority Data

Mar. 11, 2009  (FR) ...................................... 09 01122

(51) Int. Cl.
*A62B 7/00* (2006.01)

(52) U.S. Cl. ......... 128/205.11; 128/204.21; 128/204.24; 128/205.24

(58) Field of Classification Search ............. 128/204.18, 128/204.21–204.22, 204.24–204.26, 205.11–205.12, 128/205.24

See application file for complete search history.

(56) References Cited

U.S. PATENT DOCUMENTS

| | | | |
|---|---|---|---|
| 5,036,847 A | | 8/1991 | Boussignac |
| 6,152,132 A | * | 11/2000 | Psaros ...................... 128/204.25 |
| 6,450,164 B1 | * | 9/2002 | Banner et al. ............ 128/204.21 |
| 6,516,801 B2 | * | 2/2003 | Boussignac .............. 128/204.24 |
| 6,814,075 B2 | * | 11/2004 | Boussignac .............. 128/204.24 |
| 7,717,113 B2 | * | 5/2010 | Andrieux .................. 128/204.23 |
| 2002/0049753 A1 | * | 4/2002 | Burrows ........................... 707/3 |
| 2004/0050389 A1 | | 3/2004 | Boussignac |
| 2010/0229865 A1 | * | 9/2010 | Boussignac .............. 128/205.24 |

FOREIGN PATENT DOCUMENTS

| | | |
|---|---|---|
| EP | 0 390 684 | 10/1990 |
| WO | 03/039638 | 5/2003 |

* cited by examiner

*Primary Examiner* — Lynne Anderson
(74) *Attorney, Agent, or Firm* — Dickinson Wright PLLC

(57) ABSTRACT

Disclosed is a tubular device for respiratory assistance. The device includes a main channel and at least one auxiliary channel connected to a source of breathable gas. The device includes structure for diverting a volume fraction of the breathable gas intended for the auxiliary channel, and structure for aspirating ambient air that is driven by the diverted fraction of breathable gas. The structure of the device is configured such that the aspirated ambient air is mixed with the diverted fraction of breathable gas and is conveyed into the main channel between the distal orifice of the auxiliary channel and the distal end of the main channel.

8 Claims, 6 Drawing Sheets

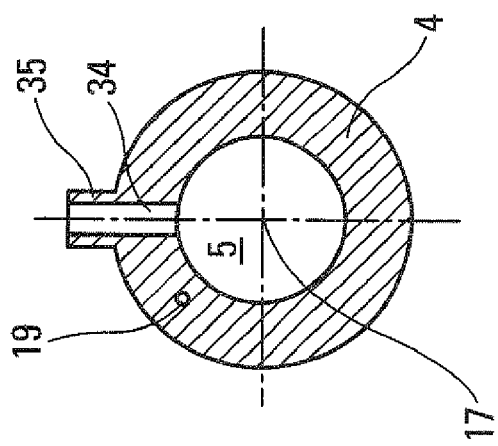
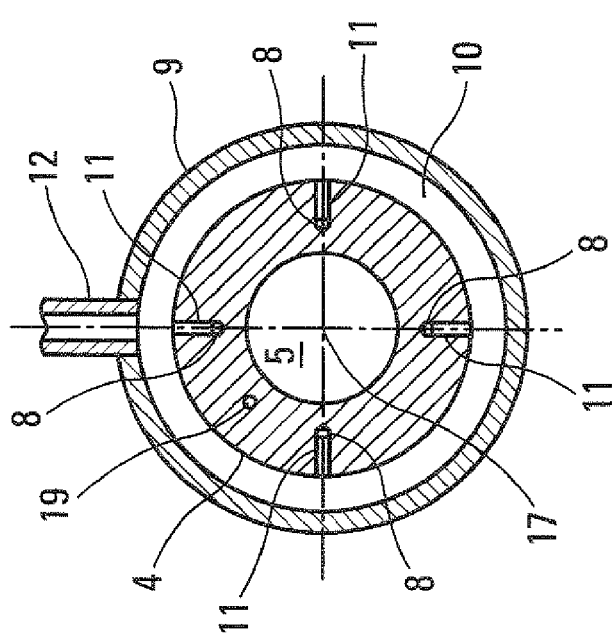
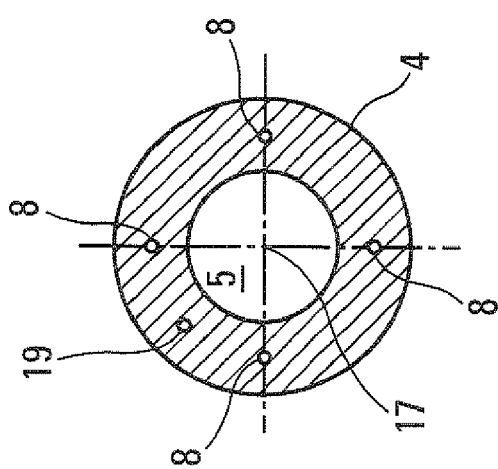

DEVICE FOR RESPIRATORY ASSISTANCE

FIELD OF THE INVENTION

The present invention relates to a device for respiratory assistance that can be used on patients whose spontaneous respiration is absent or insufficient, whether or not said patients are under artificial respiration.

BACKGROUND OF THE INVENTION

A device for respiratory assistance is already known from the patent EP-A-0390684 and comprises:
- a tube which forms a main channel and which is designed to be connected by its distal end to a respiratory airway of a patient such that said main channel connects the respiratory system of said patient to the outside; and
- at least one auxiliary channel, made for example in the wall of said tube and allowing injection of a stream of breathable gas intended to ventilate the patient, this auxiliary channel emerging into the main channel in front of the distal end of the latter.

In such a device, the breathable gas feeding the auxiliary channel is in most cases pure oxygen. However, some patients whose bodies are accustomed to a high level of carbon dioxide in the blood cannot tolerate ventilation with pure oxygen, which would lead to a risk of heart problems.

Therefore, in order to overcome this drawback, it has already been proposed, in the document EP-A-1441791, to use a respiratory assistance device of this kind that additionally comprises, between the distal orifice of the auxiliary channel and the distal end of the main channel, controllable means of fluid communication which, in the open position, are able to form a passage of variable cross section connecting said main channel to the external environment, in such a way that external air is aspirated through the means of communication by the stream of breathable gas of the main channel. The air thus introduced dilutes the breathable gas, which can then be tolerated by those patients referred to above.

The aspiration of external air arises from the vacuum generated by the stream of breathable gas in the main channel, downstream of the distal orifice of the auxiliary channel. However, the vacuum created proves not only to be low but also very unstable. This is because it is subject to variations that are unpredictable and difficult to control and that cause irregular aspiration of outside air.

Moreover, the person operating the respiratory assistance device on the patient may be forced to continually adjust the variable cross section of the passage formed by the means of communication (and thus the strength of the aspiration) in order to ensure that the dilution of the respiratory gas by the air remains substantially constant in the main channel.

SUMMARY OF THE INVENTION

The object of the present invention is to overcome these drawbacks.

To this end, according to the invention, the tubular device for respiratory assistance which forms a main channel designed to be connected by its distal portion to a respiratory airway of a patient such that said main channel connects the respiratory system of said patient to the outside, said device comprising:
- at least one auxiliary channel connected to a source of breathable gas in order to be able to blow a stream of such breathable gas through at least one distal orifice arranged in front of the distal end of said main channel; and
- means of fluid communication arranged between said distal orifice of said auxiliary channel and said distal end of said main channel, is noteworthy in that
said device for respiratory assistance comprises:
- means of diversion for diverting a volume fraction of said breathable gas coming from said source and intended for said auxiliary channel, before it enters the latter; and
- means of aspiration of ambient air which are driven by said diverted fraction of breathable gas;
and said means of aspiration are connected to said means of communication in such a way that the latter are able to convey the aspirated ambient air, mixed with said diverted fraction of breathable gas, into said main channel.

Thus, by virtue of the present invention, the diverted fraction of breathable gas drives the means of aspiration, which create an aspiration of ambient air, this aspiration being all the more important the greater the diverted fraction of breathable gas. In addition, since the diverted fraction of breathable gas is not subject to sudden and unpredictable variations (as the flow of breathable gas from the gas source is continuous and constant), there is no risk of unstable and irregular aspiration of outside air. Moreover, the diverted fraction of breathable gas is mixed with the aspirated ambient air, such that the breathable gas is diluted before arriving in the main channel.

It will thus be noted that, in the present invention, the aspiration of ambient air does not depend on the internal vacuum prevailing within the main channel downstream of the distal orifice of the auxiliary channel; it is created intentionally by the means of aspiration.

Preferably, the device for respiratory assistance comprises means of regulating said fraction of breathable gas diverted by said means of diversion, which regulating means are advantageously arranged between said means of diversion and said means of aspiration. These regulating means can comprise at least one valve.

Thus, it is possible to regulate the diverted fraction of breathable gas so as to adapt the strength of aspiration generated by the means of aspiration (which are driven by the diverted fraction of gas) and, consequently, the volume of ambient air aspirated. In this way it is possible to adjust the dilution of the diverted breathable gas.

It should be noted that the invention provides for the valve of the regulating means to be calibrated so as to be able to precisely control the volume of ambient air aspirated and, consequently, the dilution of the diverted breathable gas.

Preferably, the device for respiratory assistance comprises means of adjusting the flow rate of diluted breathable gas coming out from said means of aspiration and intended to enter said main channel. These means of adjusting the flow rate are advantageously arranged between said means of aspiration and said means of fluid communication. In addition, the means of adjusting the flow rate can comprise at least one valve.

It is thus possible to adjust the flow rate (and therefore the quantity) of diluted breathable gas entering said main channel by way of said means of communication.

In the same way as for the valve of the regulating means, it is also possible to calibrate the valve of the adjusting means in order to know precisely the quantity of diluted breathable gas introduced into the main channel.

Advantageously, said means of fluid communication comprise at least one communication orifice which is formed in the wall of said device.

Moreover, in one embodiment of the invention, means of deflecting said stream of ventilating breathable gas toward the axis of said main channel are provided opposite said distal orifice of said auxiliary channel, and said means of communication are arranged between said means of deflection and said distal end of said main channel.

BRIEF DESCRIPTION OF THE DRAWINGS

The figures in the attached drawing will show clearly how the invention can be implemented. In these figures, identical references denote similar elements.

FIGS. 2, 3 and 4 are schematic cross sections along lines II-II, III-III and IV-IV, respectively, in FIG. 1.

DETAILED DESCRIPTION OF THE INVENTION

Figure 1:
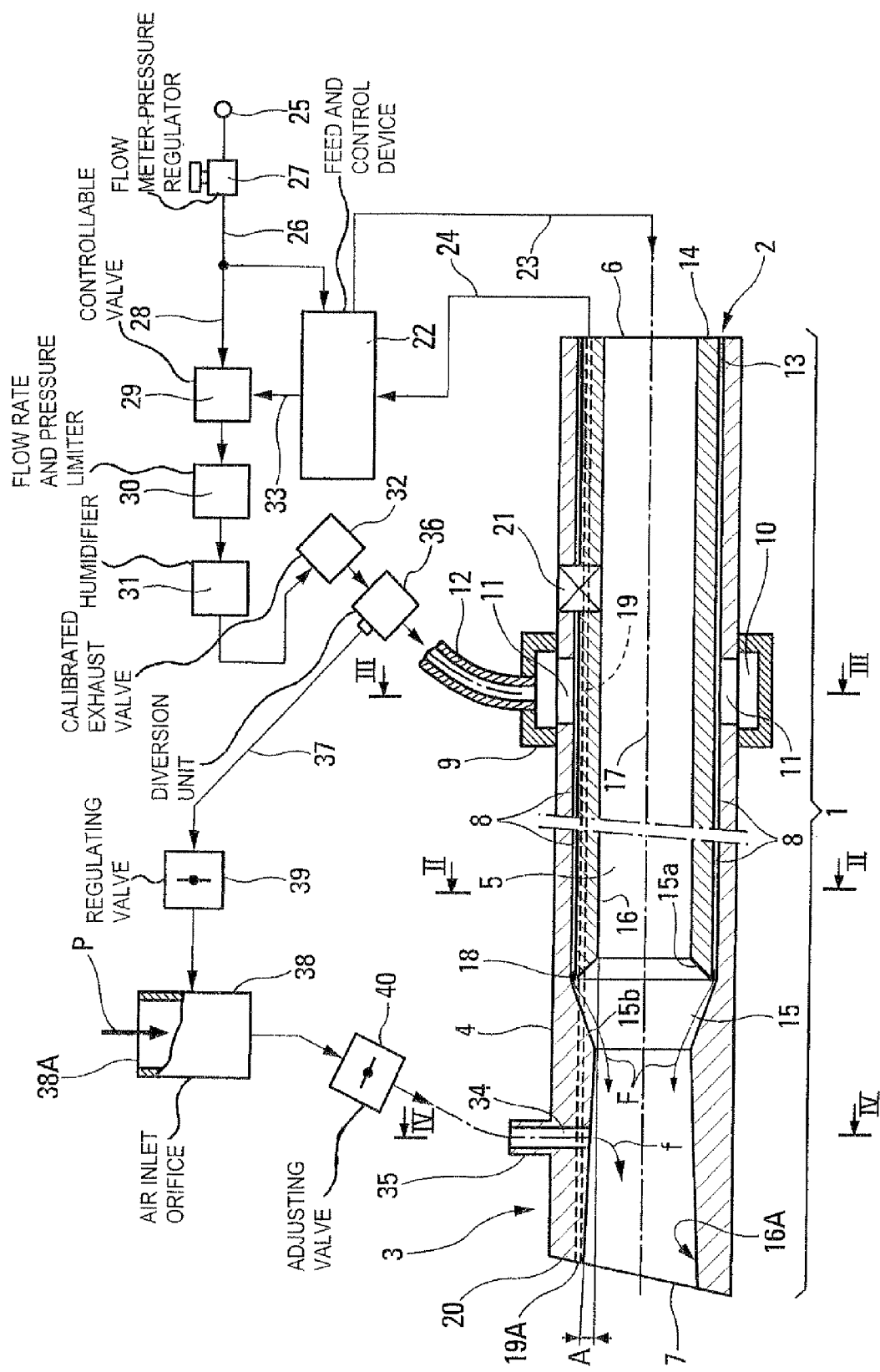
FIG. 1 is a schematic and partial view, in enlarged axial section, of a first illustrative embodiment of the device for respiratory assistance of the present invention.

FIG. 1 shows, schematically and on a large scale, only the proximal portion 2 and distal portion 3 of a first illustrative embodiment of the device 1 for respiratory assistance according to the present invention. This first illustrative embodiment can, for example, constitute an oronasal endotracheal probe with or without balloon, a pediatric endotracheal probe, a probe for gas monitoring, an endobronchial probe, an anatomical intubation probe for children, a Cole neonatal probe, a Gedel cannula probe, a nasal probe for oxygen therapy, a nasal or bucconasal mask or a nasal balloon for treatment of sleep apnea.

The device 1 comprises a tube 4 which is flexible or preshaped (to adapt to the morphology of the patient) and which delimits a main channel 5 with a proximal orifice 6 and a distal crifice 7, respectively, at the ends of said tube 4.

Thus, the main channel 5 is able to ensure a passage between the proximal orifice 6 and distal orifice 7, one of which (the distal orifice 7) is intended to be located within the respiratory airways of a patient, while the other (the proximal orifice 6) is intended to be located outside said patient. This proximal orifice 6 can open to the ambient air, and in this case the patient can inhale fresh air and exhale contaminated air through the main channel 5. As is explained below, it is also possible to connect the orifice 6 to a source of breathable gas under pressure and to provide a system of unidirectional valves, such that the patient inhales the breathable gas from said source by said main channel 5 and exhales the contaminated gas to the ambient air, also by this main channel 5.

The diameter of the main channel 5 is of the order of a few millimeters, Satisfactory trials have been carried out with diameters of 3 mm, 7 mm, 8 mm and 12 mm.

Moreover, auxiliary channels 8 are formed within the thickness of the wall of the tube 4, said auxiliary channels 8 extending over almost the entire length of the main channel 5 and being intended to be connected to a source of breathable gas under pressure, as is described below.

The connection to the source of breathable gas can be effected by way of a ring 9, surrounding the tube 4 in a leaktight manner toward the proximal end 2 and delimiting a sealed annular chamber 10 around said tube 4. The auxiliary channels 8 are brought into communication with the annular chamber 10 by way of local cuts 11 made in the wall of the tube 4, and said chamber 10 is connected to said source of breathable gas by a conduit 12. Of course, the proximal ends of the channels 8 are closed off, for example by stoppers 13 introduced from the proximal end face 14 of the tube 4.

The auxiliary channels 8 have a smaller diameter than that of the main channel 5. The diameter of the auxiliary channels 8 is preferably less than 1 mm and is advantageously of the order of 5 to 800 microns. At the distal end, the auxiliary channels 8 emerge in a recess 15 in the inner wall 16 of the tube 4. The recess 15 is annular and centered on the axis 17 of said tube 4. It comprises a face 15a, which is substantially transverse or slightly inclined in such a way as to constitute a flare in the main channel 5 into which said auxiliary channels 8 open via their orifices 18, and also a face 15b following on from the face 15a and converging in the direction of the axis 17.

Preferably, between the converging inclined face 15b and the distal orifice 7, the inner wall 16 of the tube 4 has a part slightly flared outward, as is illustrated by the angle A in FIG. 1.

Thus, when the auxiliary channels 8 are fed with breathable gas under pressure through the elements 9 to 12, the corresponding streams of gas come up against the inclined face 15b, which deflects them in the direction of the axis 17 (arrow F in FIG. 1), generating in the vicinity of the latter a pressure zone that enhances the circulation of gas inside the main channel 5 from the proximal orifice 6 toward the distal orifice 7. This enhances the patient's inhalation.

At least one supplementary channel 19 is provided within the thickness of the tube 4 and opens at 19A near the distal end face 20 of the tube 4 and serves as a pressure take-off.

For safety reasons, a calibrated exhaust valve 21 can be provided near the proximal portion 2 of the tube 4. Thus, in the event of an accidental overpressure in the main channel 5, an leakage of gas occurs outside the patient, through the wall of the tube 4, in order to eliminate this overpressure instantaneously.

As is shown in FIGS. 2 and 3, the auxiliary channels 8 are arranged regularly around the axis of the tube 4. Their number is variable depending on the applications (adult or child) but is generally between three and nine. Moreover, at least one of the auxiliary channels 8 can be specialized to provide a medical fluid.

The tube 4 of the device 1 according to the invention can be made of any material already used in respiratory probes, for example polyvinyl chloride, with an optional coating of silicone or steel to allow high-pressure injections.

Of course, the dimensions of the device 1 according to the invention can vary greatly, depending principally on the airway in which the tube is placed and on the size of the patient, who can be an adult, a child, an infant or a premature baby.

The device 1 moreover comprises a feed and control device 22 which is connected to the proximal orifice 6 of the tube 4 by a connection 23 and to the supplementary channel 19 by a connection 24.

The feed and control device 22 is fed with breathable gas under pressure, for example pure oxygen, by a source 25, to which it is connected by a conduit 26 on which an adjustable flow meter-pressure regulator 27 is mounted.

The outlet from the flow meter-pressure regulator 27 is connected to the conduit 12 via a branch conduit 28 on which there are mounted in series a controllable valve 29, an adjustable pressure drop device 30 limiting the flow rate and pressure (for example a tube with calibrated conduit), a humidifier 31, and a calibrated exhaust valve 32 whose calibration can be regulated. The controllable valve 29 is controlled by the feed and control device 22 by way of a connection 33.

By way of nonlimiting example, the flow meter-pressure regulator 27 can deliver, into the conduit 28, the breathable gas coming from the source 25 at a pressure P, for example equal to 3.5 bar with a maximum adjustable flow rate of, for example, 32 liters per minute, while the flow rate and pressure limiter 30, receiving this breathable gas from the conduit 28, can lower the pressure thereof to a value p, for example equal to 0.5 bar for an adult and to 0.07 bar for a child, and can lower the flow rate to a value d, for example equal to 0.5 liter per minute. As for the exhaust valve 32, it is calibrated to the pressure p.

Moreover (see FIGS. 1 and 4), between the annular recess 15 and the distal orifice 7, the wall of the tube 4 is provided with a communication orifice 34 which is continued radially outside the tube 4 by a gas inlet stub 35, the orifice 34 and the inlet stub 35 forming means of fluid communication to the device 1.

As is shown in FIG. 1, between the exhaust valve 32 and the ring 9 of the tube 4, means 36 for diverting a volume fraction of the breathable gas (coming from the source 25) are mounted on the conduit 12. The means of diversion 36 (shown schematically by a box in FIG. 1) can, for example, comprise a T-shaped or Y-shaped diversion element. Of course, it is also conceivable for the means of diversion to be configured differently, for example by arranging them on the branch conduit 28.

The output of the means of diversion 36 of the conduit 12 is connected to the gas inlet stub 35 by a branch conduit 37 on which means of aspiration 38 of ambient air are mounted between the means of diversion 36 and the inlet stub 35.

These means of aspiration 38, operating on a principle similar to that of an impeller pump, for example, are driven by the fraction of breathable gas diverted from the conduit 12 and coming from the source 25. They are thus able to pump ambient air (symbolized by the arrow P) through an air inlet orifice 38A. At the outlet of the means of aspiration 38, the diverted breathable gas is diluted by the aspirated ambient air.

As is shown in FIG. 1, a regulating valve 39, able to regulate the diverted fraction of breathable gas, is mounted on the branch conduit 37 between the means of diversion 36 and the means of aspiration 38. Thus, by adjusting the diverted fraction of breathable gas, the regulating valve 39 makes it possible to adjust the strength of the aspiration generated by the means of aspiration 38 (which are driven by said diverted fraction) and, consequently, the volume of aspirated ambient air.

Advantageously, the regulating valve 39 can be calibrated so as to be able to precisely control the volume of ambient air aspirated and, consequently, the dilution of the diverted breathable gas.

As is illustrated in FIG. 1, an adjusting valve 40 can also be mounted on the branch conduit 37, between the means of aspiration 38 and the gas inlet stub 35 of the tube 4. For its part, this adjusting valve 40 is able to adjust the flow rate of diluted breathable gas entering the main channel 5 (see arrow f) through the orifice 34.

The modes of operation of the device 1 according to the first illustrative embodiment (FIGS. 1 to 4) are the following:

in the artificial respiration mode, the regulating valve 39 and adjusting valve 40 are closed and the feed and control device 22, on the one hand, controls the controllable valve 29 to close by way of the connection 33, such that the conduit 12 is not fed with breathable gas, and, on the other hand, directs breathable gas into the tube 4 by way of the connection 23. This device 22 comprises means (not shown) by which it is possible to regulate the pressure and flow rate of the breathable gas which it receives from the conduit 26 and which it conveys to the tube 4. If an overpressure occurs in the respiratory tract of the patient, it is detected and transmitted, by the supplementary channel 19 and the connection 24, to the device 22, which stops operating. Moreover, if this overpressure exceeds the calibration threshold of the calibrated valve 21, for example because the supplementary channel 19 is obstructed by mucus and has not been able to transmit the overpressure information to the device 22, this valve 21 opens and the main channel 5 is connected to the atmosphere;

in the respiratory assistance mode, the feed and control device 22 cuts off the connection 23 in order to bring the proximal orifice 6 into communication with the atmosphere and controls the controllable valve 29 by the connection 33 such that it conveys to the patient a continuous or pulsed stream of breathable gas by way of the limiter 30, the humidifier 31, the calibrated exhaust valve 32, the means of diversion 36, and the auxiliary channels 8. Moreover, the regulating valve 39 and adjusting valve 40 are open. Consequently, ambient air is aspirated by the means of aspiration 38 (see arrow P) and mixed with the breathable gas (diverted by the means of diversion 36 from the conduit 12) which is thus diluted. Of course, the rate of dilution of the diverted breathable gas depends on the aspiration of ambient air by the means of aspiration 38 and therefore on the opening of the regulating valve 39. It will be noted that, for constant conditions of injection of breathable gas into the conduit 12, the rate of dilution corresponding to the opening of the regulating valve 39 can be calibrated once and for all, with the result that a patient can be fed with the most appropriate mixture of air and breathable gas by selecting a given degree of opening of this regulating valve 39. In addition, the flow rate of diluted breathable gas entering the main channel by the orifice 34 can be controlled with precision by way of the adjusting valve 40. If an overpressure occurs in the respiratory tract of the patient, as has been described above, this overpressure is detected and transmitted by the supplementary channel 19, such that the device 22 closes the controllable valve 29 and such that the conduit 28 stops conveying gas to the patient. If the supplementary channel 19 is obstructed, the device 22 is not warned of the overpressure in the patient's respiratory tract and cannot stop, but this overpressure causes an increase of pressure in the auxiliary channels 8 and the conduit 12. When this increase in pressure reaches the opening threshold of the safety valve 32, the latter opens and the stream of breathable gas is no longer conveyed to the patient and instead is diverted to the outside by said safety valve 32. Thus, although the safety means 19A, 19, 24, 22, 29 has not been able to function in this case, the stream of breathable gas cannot reach the respiratory system of the patient.

Figure 5:
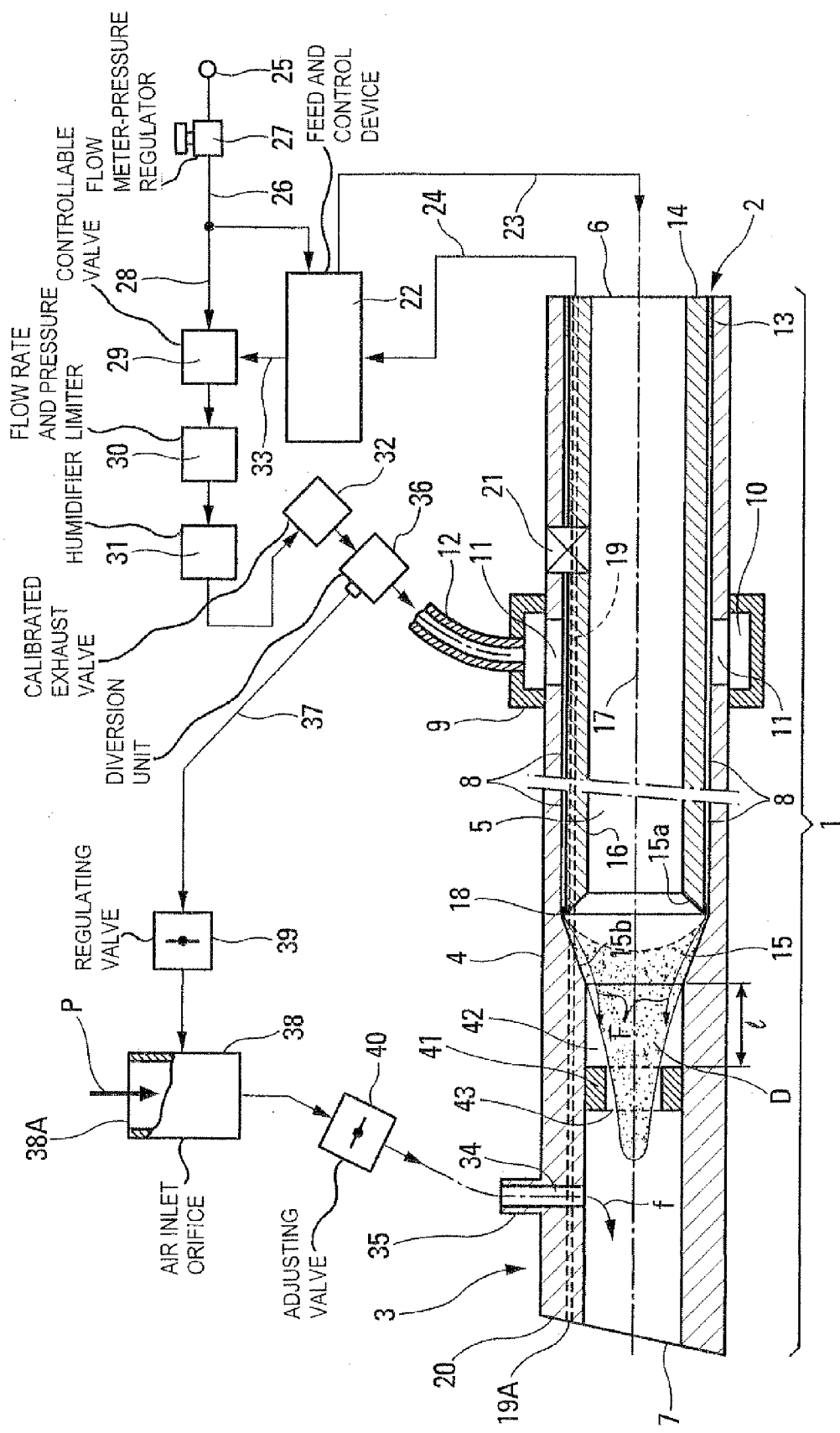
FIG. 5 shows a variant of the first illustrative embodiment of the device of the invention from FIG. 1.

It should be noted that, in a variant of the first illustrative embodiment, which variant is shown in FIG. 5 and whose function is identical to that described above, a downstream ring 41 is arranged in the distal portion 3 of the tube 4, between the annular recess 15 and the orifice 34 of the means of fluid communication. This ring 41 surrounds the central pressure zone of the main channel 5 (designated by D in FIG. 5) and at least partly occupies the annular peripheral space 42 between said central pressure zone D and the inner wall 16 of the distal portion 3 of the main channel 5.

By virtue of such a ring 41, the pressure of the source 25 of breathable gas necessary for obtaining the oblong pressure zone D can be lowered while at the same time obtaining a pressure zone D of identical pressure.

As a general rule, the distance 1 between the ring 41 and the inclined deflecting face 15b is close to the diameter of the distal part of the main channel 5.

However, in order to obtain the required optimal reduction of pressure of the source 25, it may be advantageous for this distance 1 to be adjustable. It is also advantageous, for the same reason, for the diameter of the central opening 43 of the ring 41 to be adjustable.

As is shown in FIGS. 6 to 9, the device for respiratory assistance according to the second illustrative embodiment of the invention is a tubular connector piece 1.1 which comprises an inner passage 44 and a conical wall 45 projecting into said inner passage 44.

The inner passage 44 is delimited by a proximal orifice 46 and by a distal orifice 47 at the proximal end 48 and distal end 49, respectively, of said tubular connector 1.1.

The purpose of the conical wall 45 is to deflect, in the direction of the longitudinal axis 50 of the inner passage 44, the streams of breathable gas that are injected through auxiliary channels 51 and fed from an orifice 52 continued by a lateral intake stub 53, by way of a peripheral annular chamber 54. The streams of breathable gas, originating from a source 25 of breathable gas, emerge of the auxiliary channels 51 by the orifices 51A thereof.

The intake stub 53 is connected to means of diversion 36 (similar to those described above in relation to FIG. 1) by a conduit 12.

Moreover, near its distal portion 48, the wall of the tubular connector 1.1 is provided with a communication orifice 34 which is continued radially outward by a lateral gas inlet stub 35, and the orifice 34 and stub 35 form means of fluid communication with the device 1.1.

These means of fluid communication can be fed with diluted breathable gas by a diversion conduit 37, by way of the means of diversion 36, a regulating valve 39, means of aspiration 38, and an adjusting valve 40 (described above in relation to FIG. 1).

Moreover, the tubular connector 1.1 comprises a tubular central portion 55 which is interposed between the proximal portion 48 and the distal portion 49 and of which the distal longitudinal end 55A projects slightly into the inner passage 44 in such a way as to form a downstream ring with a function similar to that of the aforementioned downstream ring 41.

Exhaust orifices 56 are formed in the lateral wall of the middle portion 55 in such a way as to connect the inner passage 44 to the ambient air. These exhaust orifices 56 are preferably distributed uniformly about the axis 50, on the same section of the middle portion 55. They make it easier for the patient to exhale by allowing contaminated gas to escape from the respiratory system of said patient.

The exhaust orifices 56 can also be covered by a ring 56A which is able to turn gently around the middle portion 55 and is itself provided with holes 56B whose diameter is at least equal to that of the orifices 56 and which can be disposed opposite the orifices 56 by rotating the ring 56A.

Moreover, at the distal portion 49, the tubular connector 1.1 comprises an annular peripheral chamber 60 arranged coaxially with respect to said connector 1.1. The annular peripheral chamber 60 emerges at the distal end 47 of the connector 1.1 and is provided, at its proximal end, with an outlet stub 61, which can be connected to a gas analyzer and to a pressure measurement device (neither of which is shown).

A fibrous or porous filter 62 is arranged in the annular peripheral chamber 60 in order to attenuate the gas turbulence and, consequently, excessive pressure variations.

Figure 6:
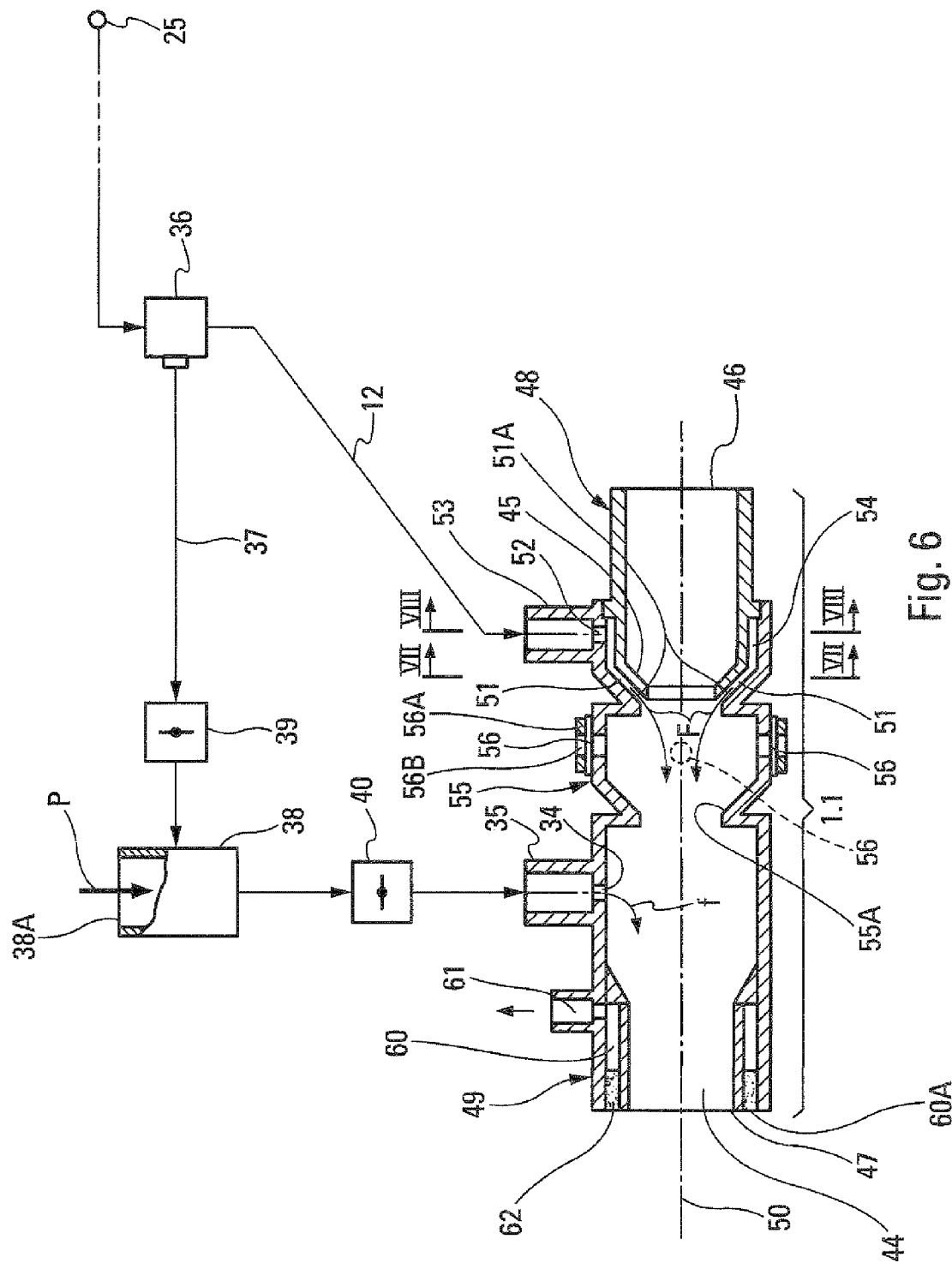
FIG. 6 is a schematic view, in enlarged axial section, of a second illustrative embodiment of the device for respiratory assistance according to the invention.
Figure 8:
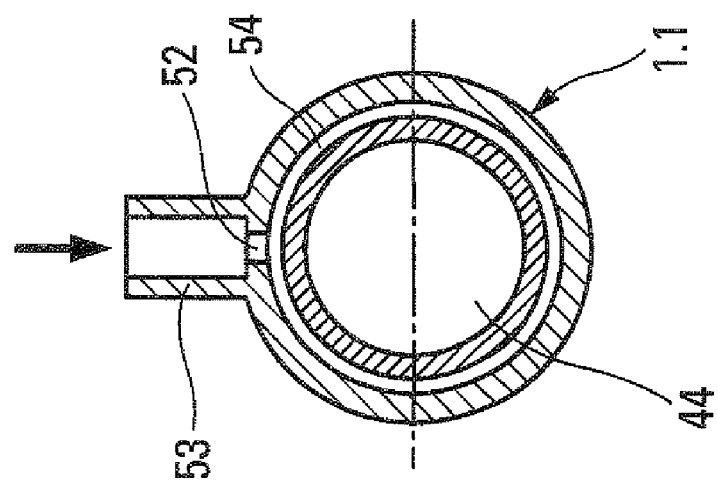
FIGS. 7 and 8 are schematic cross sections through the device from FIG. 6, along lines VII-VII and VIII-VIII, respectively.
Figure 7:
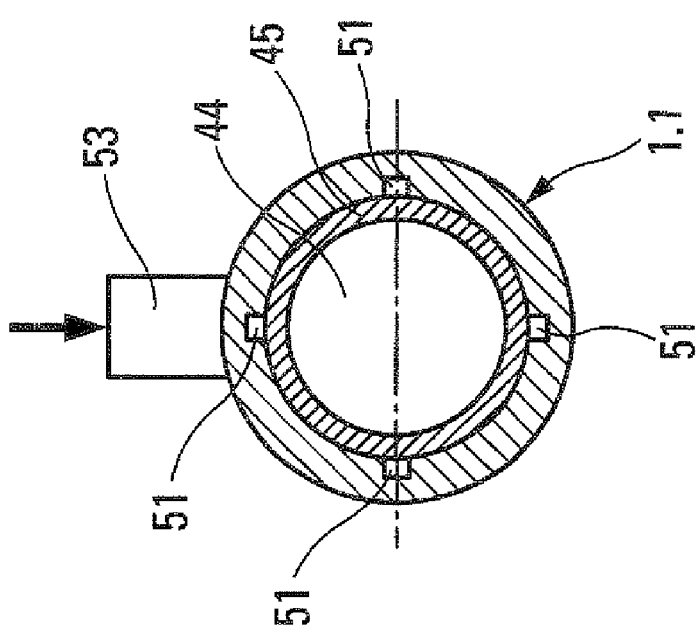

Although they have not been shown in FIGS. 6 to 8, it goes without saying that the tubular connector 1.1 can comprise channels or conduits for injection of medicaments and/or water.

Figure 9:
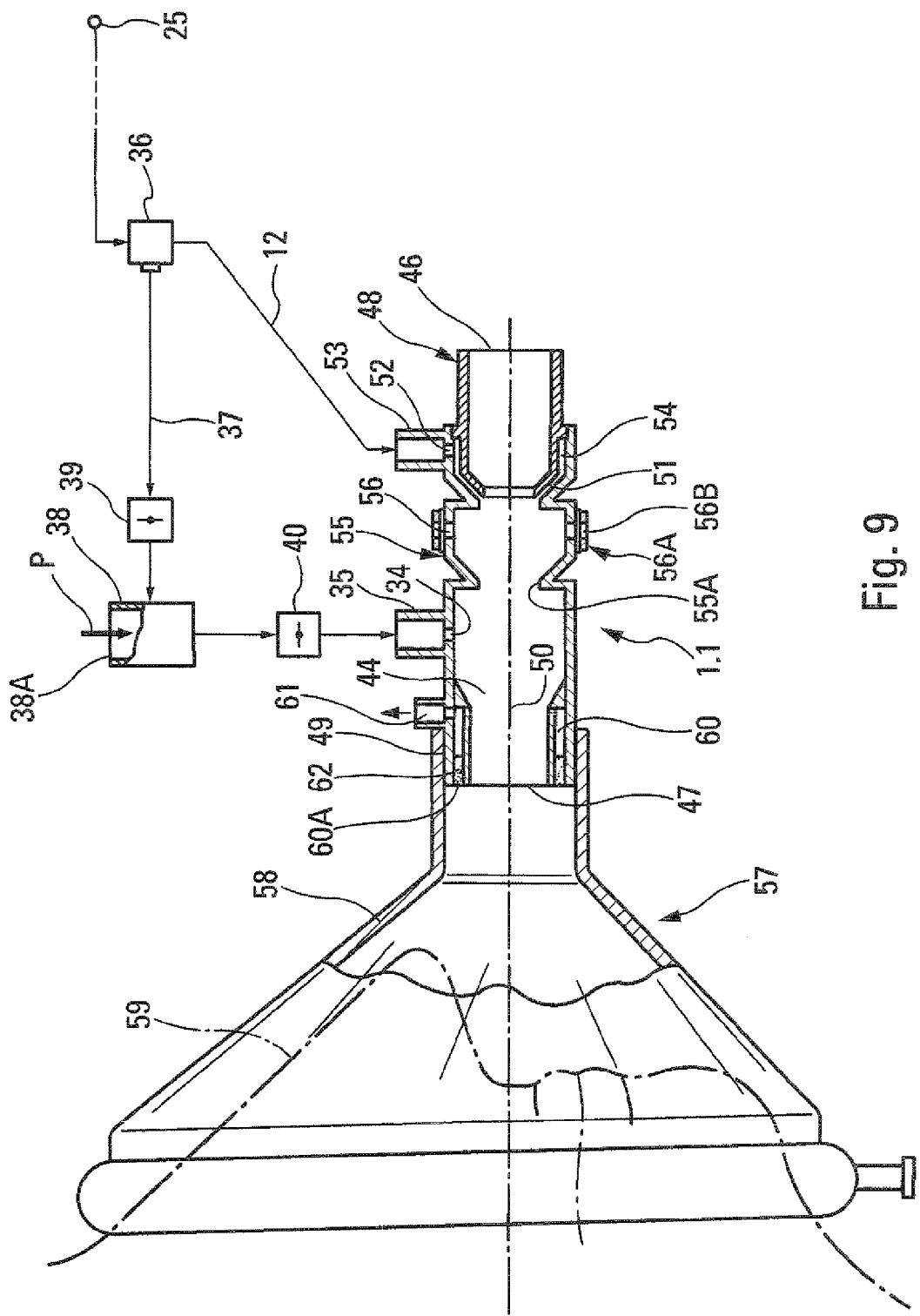
FIG. 9 is a schematic view, partially in axial section, of a respiratory assistance mask comprising the device of the invention illustrated in FIG. 6.

FIG. 9 shows a respiratory assistance mask 57 which comprises a rigid shell 58 of general truncated cone shape and which can be fitted on the face of a patient 59. At the opposite end, said mask 57 comprises the tubular device 1.1 according to the second illustrative embodiment of the present invention. This tubular device 1.1 serves as a connector through which gas enters and leaves the mask 57.

Of course, it will be readily appreciated that the device 1.1 according to the second illustrative embodiment is not limited to the particular use of the respiratory mask (FIG. 9) and can have numerous other uses, for example as a nasal probe, oral probe, tracheal probe, laryngeal mask, King system, Combitube (registered trademark), etc. It is obvious that the dimensions of said device are then adapted to each particular use.

The invention claimed is:

1. A tubular device for respiratory assistance which forms a main channel designed to be connected by its distal end to a respiratory airway of a patient such that said main channel connects the respiratory system of said patient to the outside, said device comprising:

at least one auxiliary channel connected to a source of breathable gas in order to be able to blow a stream of such breathable gas through at least one distal orifice arranged in front of the distal end of said main channel; and fluid communication means which are arranged between said distal orifice of said auxiliary channel and said distal end of said main channel, wherein said device for respiratory assistance further comprises:

diversion means for diverting a volume fraction of said breathable gas intended for said auxiliary channel, before said breathable gas enters the auxiliary channel;

aspiration means for aspirating ambient air, driven by said diverted fraction of breathable gas, wherein said aspiration means are connected to said fluid communication means so that the fluid communication means is configured to convey the aspirated ambient air, mixed with said diverted fraction of breathable gas, into said main channel; and regulating means for regulating said fraction of breathable gas diverted by said diversion means.

2. The device as claimed in claim 1, wherein said regulating means are arranged between said diversion means and said aspiration means.

3. The device as claimed in claim 1, wherein said regulating means comprise at least one valve.

4. The device as claimed in claim 1, wherein the device additionally comprises adjusting means for adjusting flow rate of diluted breathable gas coming out from said aspiration means and entering said main channel.

5. The device as claimed in claim 4, wherein said adjusting means for adjusting the flow rate are arranged between said aspiration means and said fluid communication means.

6. The device as claimed in claim 4, wherein said adjusting means for adjusting the flow rate comprise at least one valve.

7. The device as claimed in claim 1, wherein said fluid communication means comprise at least one communication orifice which is formed in a wall of said device.

8. The device as claimed in claim 1, wherein deflecting means for deflecting said stream of ventilating breathable gas toward an axis of said main channel are provided opposite said distal orifice of said auxiliary channel, and said fluid communication means are arranged between said deflection means and said distal end of said main channel.

* * * * *